United States Patent [19]
Olerud

[11] Patent Number: 5,735,853
[45] Date of Patent: Apr. 7, 1998

[54] BONE SCREW FOR OSTEOSYNTHESIS

[76] Inventor: Sven Olerud, Villa Malmen, S-740 11 Länna, Sweden

[21] Appl. No.: 750,708

[22] PCT Filed: Jun. 16, 1995

[86] PCT No.: PCT/SE95/00744

§ 371 Date: Dec. 16, 1996

§ 102(e) Date: Dec. 16, 1996

[87] PCT Pub. No.: WO95/35067

PCT Pub. Date: Dec. 28, 1995

[30] Foreign Application Priority Data

Jun. 17, 1994 [SE] Sweden ................... 9402130

[51] Int. Cl.[6] .................................................. A61B 17/80
[52] U.S. Cl. ............................. 606/71; 606/69; 606/73
[58] Field of Search ......................... 606/69, 70, 71, 606/72, 73, 61, 60, 86, 59

[56] References Cited

U.S. PATENT DOCUMENTS

| | | |
|---|---|---|
| 4,388,921 | 6/1983 | Sutter et al. |
| 4,484,570 | 11/1984 | Sutter et al. ................ 606/72 |
| 5,057,111 | 10/1991 | Park ............................ 606/69 |
| 5,151,103 | 9/1992 | Tepic et al. .................. 606/69 |
| 5,269,784 | 12/1993 | Mast ........................... 606/69 |
| 5,501,684 | 3/1996 | Schlapfer et al. ........... 606/73 |
| 5,520,690 | 5/1996 | Errico et al. ................ 606/61 |

FOREIGN PATENT DOCUMENTS

| 1329525 | 5/1994 | Canada. |
|---|---|---|
| 3027148 | 5/1982 | Germany. |
| WO88/03781 | 6/1988 | WIPO. |

*Primary Examiner*—Guy V. Tucker
*Attorney, Agent, or Firm*—Burns, Doane, Swecker & Mathis, L.L.P.

[57] ABSTRACT

An implant device comprises a plate element (1) with a number of bone screw holes and bone screws (3) which are insertable and lockable therein. The head portion (23) of a bone screw is adapted to be inserted in an annular hole insert (19) mounted in the associated hole, such that the bone screw (3) can be made to occupy different angular positions in relation to the plate element by rotating or tilting the hole insert (19) and the bone screw therein in relation to the hole wall (17). The head portion (23) of a bone screw is adapted, when in an unlocked state, to be retainable in the hole insert (19) in such a manner as to be nondisplaceable in the longitudinal direction but preferably be rotatable, owing to the fact that it is provided with an annular bead (27) while the cooperating inner annular surface (21) of the hole insert is formed with an annular recess (25) matching and receiving the annular bead. A bone screw hole located at one plate-element end is adapted to be displaceable as a result of being provided in a plate member (9), which is so mounted in the plate element (1) as to be translationally displaceable.

18 Claims, 2 Drawing Sheets

BONE SCREW FOR OSTEOSYNTHESIS

This application is filed under 35 USC 371 based on PCT/SE95/00744 which was filed on Jun. 16, 1995 published as WO95/35067 Dec. 28, 1995.

TECHNICAL FIELD

This invention relates to implant devices of the type comprising a plate element with a number of bone screw holes and at least two bone screws which are insertable and lockable in bone screw holes, the head portion of each bone screw being adapted to be inserted in an annular hole insert mounted in the associated hole, said hole insert having a convex, preferably at least essentially part-spherical, outer annular surface, which is adapted to cooperate with a matching concave, preferably at least essentially part-spherical hole wall surface, such that a bone screw inserted in a bone screw hole can be made to occupy different angular positions in relation to the plate element by rotating or tilting the hole insert and the bone screw therein in relation to the hole wall.

BACKGROUND ART

Implant devices of the above type are often used in orthopaedic operations, for instance with a view to stabilising fractured bones, stabilising the positions of vertebrae and reducing vertebrae.

Various solutions for imparting flexibility to the bone screws as regards their directions in relation to the plate element have been suggested. For instance, it has been suggested that the head portion of the bone screws employed should have a part-spherical outer surface adapted to cooperate with a matching hole surface in a plate element, such that the bone screw may occupy the desired angular position in relation to the plate element when screwed into the hole, this angular position being fixed when the bone screw is locked in relation to the plate element, e.g. with the aid of an inner expansion locking screw. Prior to locking, the bone screw is maintained against the plate element as a result of the application pressure obtained when the plate element is pressed against the subjacent bone.

In one variant of this type of construction, the spherical mounting enabling an alteration of the relative angular positions of the bone screw and the plate element is achieved with the aid of a special hole insert, which has a part-spherical circumferential surface and is positioned in a matching hole in the plate element and which is formed with a central through hole adapted to receive a bone screw. This latter hole thus corresponds to an ordinary bone screw hole in a plate element.

It has, however, been found desirable that the plate element should not have to be applied against the subjacent bone, pressing against it. Thus, it has also been suggested that a part-spherical head portion of a bone screw be accommodated and in itself retained in a matching hole in a plate element. However, this construction is complicated in many respects and is even practically inapplicable in certain cases, for instance when several bone screws are to be arranged in different angular positions in relation to the plate element.

OBJECTS OF THE INVENTION

One object of this invention is to provide an implant device enabling the bone screws to be applied in simpler and more expedient fashion.

Another object of the invention is to provide an implant device enabling enhanced flexibility as regards the positions of the bone screws in relation to the plate element.

Yet another object of the invention is to provide an implant device opening up new and more extensive fields of application.

SUMMARY OF THE INVENTION

According to the invention, these objects are achieved by an implant device which is of the type mentioned by way of introduction and has the distinctive features recited in the appended claims.

In a first aspect of the invention, the implant device is distinguished by the fact that the head portion of a bone screw is adapted, when in unlocked state, i.e. when not locked in relation to the plate element by means of e.g. a locking screw, to be retainable in an associated hole insert, so as to be nondisplaceable in the longitudinal direction but preferably be rotatable. In a preferred embodiment, the head portion of each bone screw is preferably cylindrical and is equipped with an annular bead, while the cooperating inner annular surface of the hole insert is also preferably cylindrical and is equipped with an annular recess matching and receiving the annular bead, or vice versa. In a construction of this type, hole inserts are easily mounted in advance in the plate element, while bone screws are expediently and at a later stage, i.e. at a suitable stage of the implant mounting procedure, caused, regardless of the angular position in relation to the plate element, to be retained in the respective hole inserts, for instance by snap-in locking when the respective bone screws are screwed into the holes. In other words, a bone screw may unhindered be screwed into the subjacent bone through the bone screw hole in the hole insert and be retained therein, when the head portion of the screw enters the hole insert and is retained by the engagement therewith. It will be appreciated that the head portion of the bone screw and/or the hole insert should be so designed that this engagement can be brought about without difficulties, for instance by resilient reduction of the diameter of the head portion of the bone screw to the extent required when the engagement means employed enter the inner bone screw passage of the hole insert.

In a second aspect of the invention, the implant device of the type mentioned in the introduction is distinguished by the fact that at least one bone screw hole equipped with a hole insert is arranged to be displaceable in the plate element, such that the position of the associated bone screw becomes highly flexible in relation to the plate element. The combination of general rotatability owing to the hole insert mounting and the displaceability along the plate element enables a bone screw to be screwed into the hole largely independently of the basic position of the plate element, and also enables the relative positions of the plate element and the screwed-in bone screw to be adjusted at a later stage. This fact may advantageously be used, for instance when reducing vertebrae.

The displaceability along the plate element, as a rule essentially in parallel with a general plane of the plate element, is advantageously achieved by providing the respective displaceable bone screw holes in a plate member, which preferably is translationally displaceable in the plate element. Advantageously, the plate member is mounted within the plate element in a groove or the like, the plate element being formed with a matching recess permitting access to the bone screw hole, regardless of the position of the plate member in the plate element.

It has now been found advantageous to provide a displaceable bone screw hole at each end of an elongate plate element. Advantageously, at least one additional bone screw hole is provided in the plate element adjacent to the respective displaceable bone screw holes. Such a bone screw hole may be of conventional design, but is preferably adapted to bone screw mounting in accordance with the first aspect of the invention mentioned above. Such additional bone screw holes enable the plate element to be fixed to the subjacent bone when displaceable bone screw holes and bone screws therein with associated, temporarily applied adjusting elements have been employed, e.g. for reducing vertebrae. After fixation involving the use of such an additional bone screw hole, the fixation may be supplemented with locking also of the bone screws in the displaceable bone screw holes, once the adjusting elements have been removed.

The above-mentioned adjusting elements, which may be in the form of rods by means of which the angular position of a screwed-in bone screw in relation to the plate element can be adjusted (in which case the position of the plate member in relation to the plate element may need some adjustment), may, for instance, be adapted to be temporarily secured to the bone screw at issue with the aid of a threaded joint in an internal, threaded bore in the bone screw.

As is no doubt obvious to those skilled in the art, it is especially advantageous to combine the two aspects of the invention accounted for above.

In the following, an embodiment of the invention will be described in more detail with reference to the accompanying drawings.

DESCRIPTION OF AN EMBODIMENT

Figure 2:
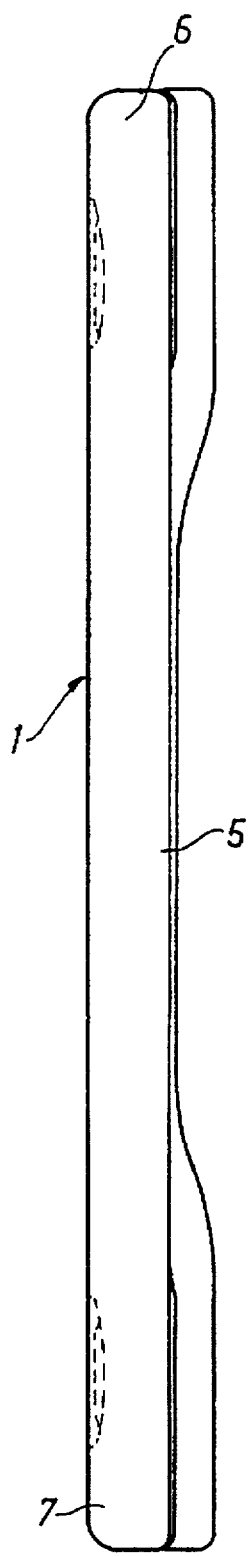
FIG. 2 is a schematic side view of the plate element shown in FIG. 1.
Figure 1:
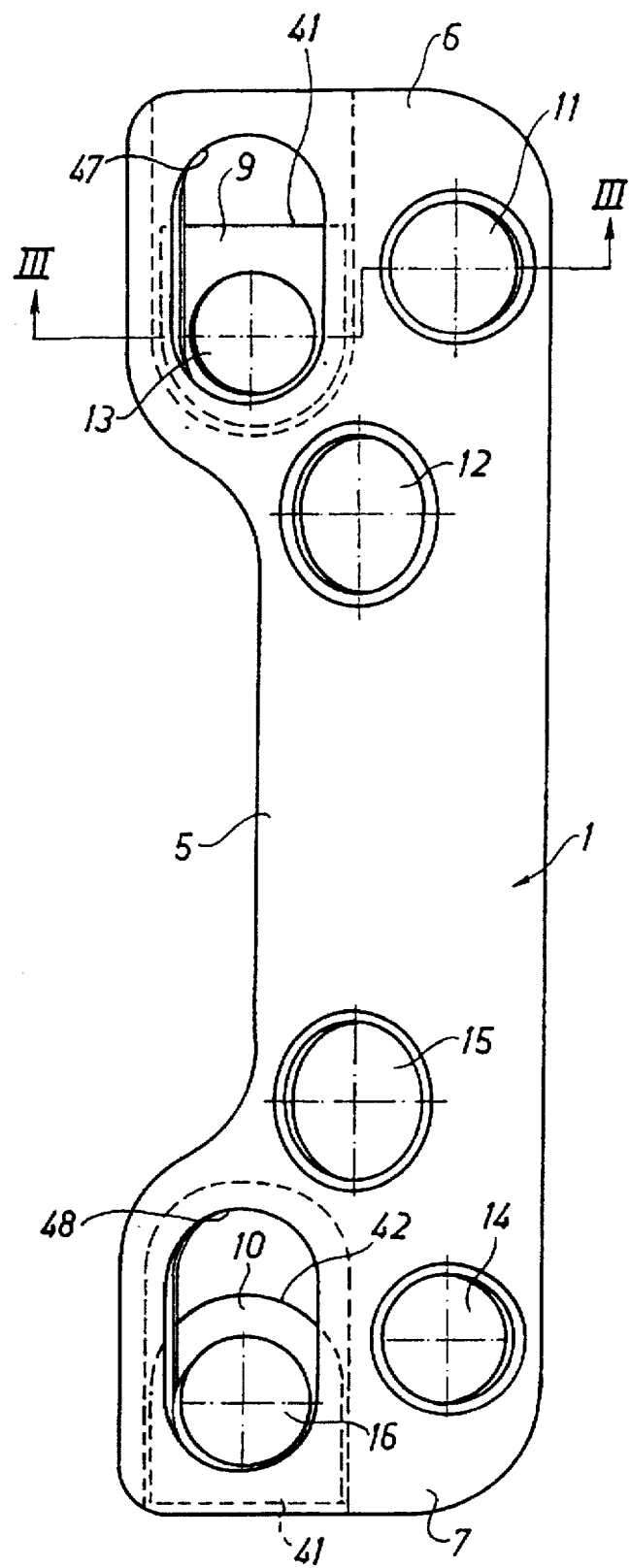
FIG. 1 is a schematic top view of an embodiment of an implant plate element in accordance with the invention.
Figure 3:
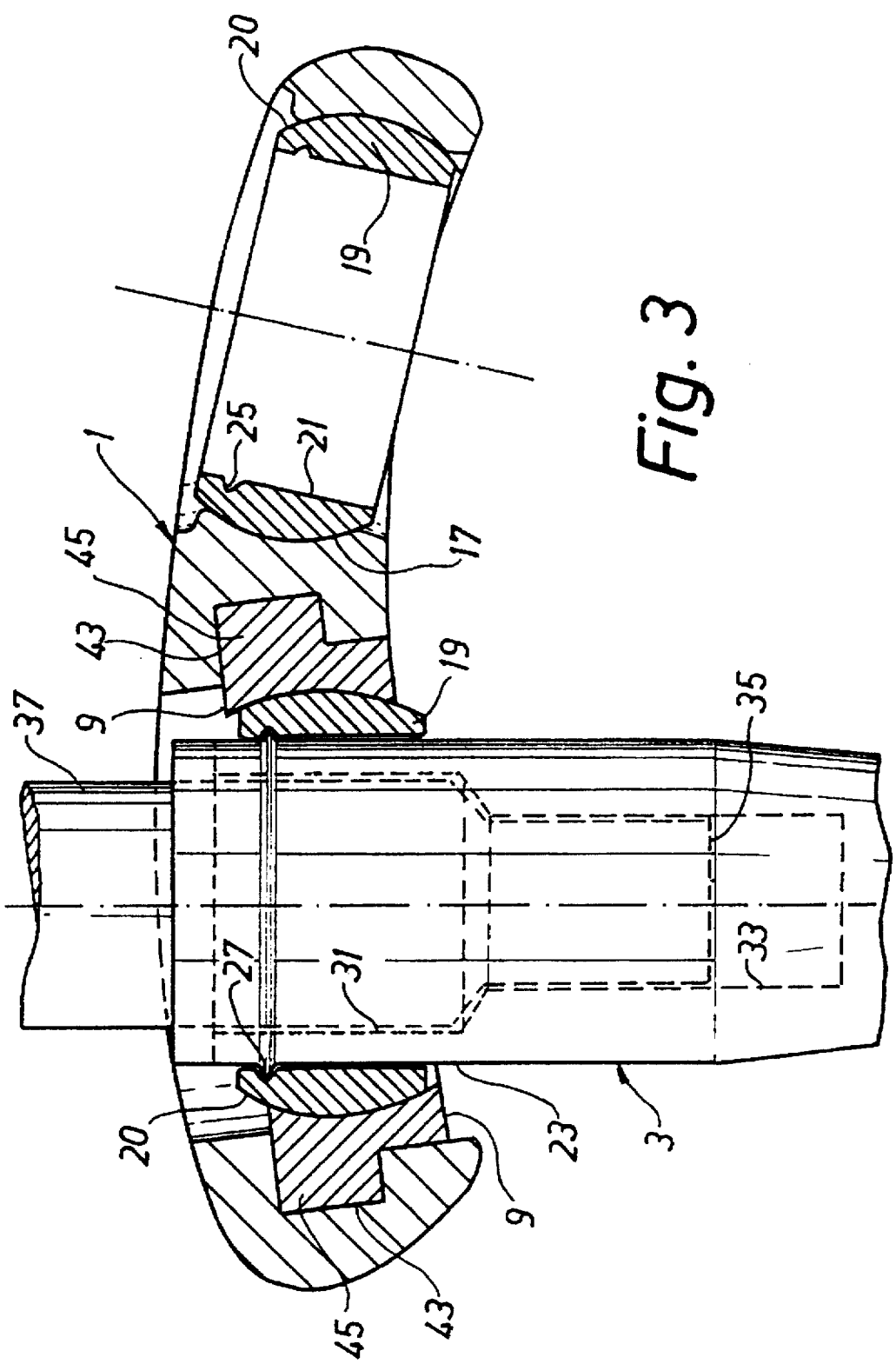
FIG. 3 is a schematic sectional view of the plate element in FIGS. 1 and 2, taken along the line III—III in FIG. 1, the holes in the plate element being provided with associated hole inserts, and an applied bone screw and an adjusting rod fixed therein being schematically shown.

FIGS. 1–3 show an example of an implant device according to the invention. This device comprises an implant plate element 1 as well as bone screws 3, which are used for fixing the implant plate element in bone, such as vertebrae, and of which but one is shown in FIG. 3. The plate element 1 is a slightly curved, elongate plate having a centre portion 5 of reduced width and two end portions 6, 7, whose one lateral half has an increased thickness in order to accommodate a movable plate member 9 and 10, respectively. The plate element 1 has six circular, identical bone screw holes 11–16, of which four holes 11, 12, 14 and 15 are stationarily arranged in the plate element 5 and two holes 13, 16 are displaceably arranged in the plate element, one in each plate member 9, 10. The bone screw holes 11, 14 are provided in the non-thickened end portion side of the plate element, while the bone screw holes 12, 15 are provided at the transition between the end portions and the centre portion of reduced width of the plate element.

Each bone screw hole has a concave, spherically curved hole wall 17 and is adapted to accommodate an annular hole insert 19 having a convex, correspondingly spherically curved circumferential surface 20 and a circular-cylindrical, inner hole wall 21 intended to cooperate with the circular-cylindrical head portion 23 of a bone screw 3.

The hole inserts 19 are, in convenient fashion (not shown), cut up and/or slit up, so that they may easily be resiliently compressed somewhat when to be inserted in the respective bone screw holes. The inserts 19 have a height that slightly exceeds that of the mounting seat formed by the hole wall 17. As is easily understood, an applied hole insert 19 may (even with an inserted, albeit not yet locked, bone screw 3) easily be rotated in relation to the plate element, not only about its own axis but also about an optional axis perpendicular thereto, i.e. it can be tilted in relation to the plate element 1. At the top, i.e. on the side facing away from the bone side, the hole inserts 19 are, on their inner hole wall, provided with a circumferential recess or groove 25, which is adapted to cooperate with a matching, preferably circumferential annular bead 27 provided on the head portion 23 of the bone screws.

It will be appreciated that a bone screw may easily be screwed through the hole of a hole insert, in which case the bead 27 will eventually snap into the groove 25. In the head portion, the bone screw may be yielding to a certain extent, so as to enable easy and smooth snap-in locking of the bead 27 in the groove 25. This can be achieved by in known manner providing the head portion of the bone screw with suitable longitudinal slits (not shown). Owing to the snap-in engagement, the bone screw 3 will be retained in the hole insert 19, such that it no longer can be displaced in the longitudinal direction in relation to the hole insert, but still is able to rotate about its longitudinal axis in relation to the hole insert.

It has been found that the groove 25 and the bead 27 may be given rather small dimensions while maintaining excellent retention. Also, this means that the snap-in locking itself is a very smooth operation (regardless of the angular position of the hole insert in relation to the plate element), resulting in expedient screwing of the bone screws 3 even in connection with complicated configurations.

The head portion 23 of the bone screws 3 has an internal, threaded bore 31 adapted to receive, in known suitable fashion, a locking means (not shown), such as a locking screw, for expansion locking of a screwed-in bone screw in relation to the hole insert and the plate element. The required expansion of the head portion 23 can be facilitated by longitudinal slits therein of the type mentioned above. Farthest out, the head portion 23 may, for instance, be provided with recesses (not shown) distributed over its circumference and adapted to engage a tool for screwing the bone screw into the associated hole in known fashion.

Furthermore, the bone screw 3 has a threaded bore 33 of reduced diameter, which is located beneath the bore 31 and is adapted to receive the threaded, diameter-reduced end 35 of an adjusting rod 37, the use of which will be described in more detail below. At the bottom, the adjusting rod 37 has a diameter corresponding to that of the bore 31 in order to produce optimum stability after the bone screw has been inserted.

As is evident from FIGS. 1 and 3, the plate members 9, 10, in which the displaceable bone screw holes 13, 16 are centrally arranged, are displaceable in line with each other and in parallel with the longitudinal axis of the plate element 1. The plate members 9, 10 are elongate and have two parallel side edges and one straight, cut end 41 and one part-circular, rounded end 42. The plate members 9, 10 are arranged in corresponding recesses formed at the underside of the plate element, these recesses extending inwards from the respective end edges of the plate element and having a rounded end portion corresponding to the rounded end 42 of the plate members. The plate members are inserted with the rounded end first in the respective recesses from the end of the plate element where the respective recesses are open.

The recesses are formed with a guiding groove 43, in which engages a matching, square guiding projection 45 from the plate members, keeping the plate member in place in displaceable fashion. The guiding projection 45 extends along the side edges and the rounded end edge of the plate members 9, 10.

In order to give access to the bone screw holes 13, 16 in the plate members 9, 10, holes 47, 48 are provided in the plate element above the plate member recesses. The holes 47, 48 are elongate and have a width slightly exceeding the diameter of the bone screw holes and further have semi-circular end portions which, as to position, correspond to the two extreme positions of the holes 13, 16 of the plate members, as appears from FIG. 1, where the plate member 9 is maximally inserted in the plate element and the plate member 10 is maximally displaced outwards (as regards function). In the latter position, the straight edge 41 of the plate member is located essentially at the end edge of the plate element.

When the plate members 9, 10 have been inserted in their respective recesses in the plate element, the hole inserts of the bone screw holes can be mounted. Owing to their height, as a result of which they project upwards beyond the upper flat surface of the plate members 9, 10, the hole inserts will then prevent the plate members from sliding out of the plate element, which is undesirable.

Typically, the implant device shown in FIGS. 1-3 is employed as follows.

The plate element 1 with mounted plate members 9, 10 is provided with hole inserts in the bone screw holes, and the two plate members are maximally inserted, such that the associated bone screw holes 13, 16 occupy an inner position, as does the hole 13 in FIG. 1. The plate element is then applied against a series of vertebrae to be reduced, and bone screws 3 are screwed into the vertebrae through the holes 13, 16 in diverging directions, until the bone screws have been locked by snap-in action in the plate element. If need be, the position of the plate element may then be adjusted in the direction of or away from the vertebrae by rotating one or both of the bone screws.

Adjusting rods 37 are then fixed in the bone screws 3 (see FIG. 3), whereupon a spacing tool is brought into engagement with the two adjusting rods. With the aid of the tool, the adjusting rods are forced apart, which means that the bone screws are straightened up in relation to the plate element, resulting in simultaneous alteration of the positions of the vertebrae into which are screwed the bone screws. This positional alteration may mean that a situation with an increased vertebral angle in the forward direction (kyphosis) changes to a situation with a slight vertebral angle in the rearward direction (lordosis). The angular alteration of the bone screws 3 in relation to the plate element 1 necessitates a simultaneous, translational displacement of the plate members 9, 10.

After the bone screws have been thus straightened up, it may be necessary to increase the distance between the bone screws, i.e. space apart the vertebrae, which, as will be appreciated, also requires that the plate members are translationally displaced in the direction away from each other.

When the aimed-at alteration of the positions of the vertebrae has been achieved, bone screws are, in a suitable direction, screwed through and locked in one or both of the two adjoining bone screw holes located adjacent to the respective plate member holes. Thereafter, the adjusting rods may be removed one at a time, and the bone screw at issue may also be locked, for instance with the aid of a locking screw. As a result, the vertebrae will be fixed in their new positions.

I claim:

1. An implant device, comprising:

a plate element, the plate element including a plurality of bone screw holes;

annular hole inserts provided in at least two of the plurality of bone screw holes;

at least two bone screws, the at least two bone screws each having a head portion that is insertable, in a longitudinal direction of the bone screw, in a hole insert of an associated one of the plurality of bone screw holes and lockable and unlockable relative to the hole insert;

the hole inserts each having a convex, substantially spherical, outer annular surface, the outer annular surface of each hole insert cooperating with a matching concave, substantially spherical wall surface of an associated one of the plurality of bone screw holes such that when one of the at least two bone screws is inserted in a hole insert of an associated one of the plurality of bone screw holes, the one of the at least two bone screws is movable to different positions relative to the plate element by rotating or tilting the hole insert and the one of the at least two bone screws inserted therein in relation to the wall surface of the associated one of the plurality of bone screw holes; and means for retaining the head portions of the at least two bone screws in associated ones of the hole inserts such that the head portions are nondisplaceable in the longitudinal direction when the head portions are in a locked condition, wherein the retaining means provide a snap-in engagement between head portions and the associated hole inserts.

2. A device as set forth in claim 1, wherein each of the plurality of bone screws is adapted to temporarily receive an adjusting element for adjusting an angular position of the bone screw (3) in relation to the plate element when the bone screw is in an unlocked condition.

3. A device as set forth in claim 1, wherein the head portion of each of the at least two bone screws is cylindrical and is provided with an annular bead, and an inner surface of an associated one of the hole inserts is cylindrical and is provided with an annular recess, the annular recess matching and receiving the annular bead.

4. A device as set forth in claim 1, wherein at least one of the plurality of bone screw holes is located at an end of the plate element and is provided with one of the hole inserts and is displaceable in the plate element.

5. An implant device, comprising:

a plate element, the plate element including a plurality of bone screw holes;

annular hole inserts provided in at least two of the plurality of bone screw holes;

at least two bone screws, the at least two bone screws each having a head portion that is insertable, in a longitudinal direction of the bone screw, in a hole insert of an associated one of the plurality of bone screw holes and lockable and unlockable relative to the hole insert;

the hole inserts each having a convex, substantially spherical, outer annular surface, the outer annular surface of each hole insert cooperating with a matching concave, substantially spherical wall surface of an associated one of the plurality of bone screw holes such that when one of the at least two bone screws is inserted in an associated one of the plurality of bone screw holes, the one of the at least two bone screws is movable to different positions relative to the plate element by rotating or tilting the hole insert and the one of the at least two bone screws inserted therein in relation to the wall surface of the associated one of the plurality of bone screw holes; and means for retaining the head portions of the at least two bone screws in associated ones of the hole inserts such that the head portions are nondisplaceable in the longitudinal direction when the head portions are in a locked condition, wherein the head portion of each of the at least two bone screws is cylindrical and is provided with an annular bead, and an inner surface of an associated one of the hole inserts is cylindrical and is provided with an annular recess, the annular recess matching and receiving the annular bead.

6. A device as set forth in claim 5, wherein the retaining means provide a snap-in engagement between the head portions and the associated hole inserts.

7. An implant device, comprising:

a plate element, the plate element including a plurality of bone screw holes;

annular hole inserts provided in at least two of the plurality of bone screw holes;

at least two bone screws, the at least two bone screws each having a head portion that is insertable, in a longitudinal direction of the bone screw, in a hole insert of an associated one of the plurality of bone screw holes and lockable and unlockable relative to the hole insert;

the hole inserts each having a convex, substantially spherical, outer annular surface, the outer annular surface of each hole insert cooperating with a matching concave, substantially spherical wall surface of an associated one of the plurality of bone screw holes such that when one of the at least two bone screws is inserted in an associated one of the plurality of bone screw holes, the one of the at least two bone screws is movable to different positions relative to the plate element by rotating or tilting the hole insert and the one of the at least two bone screws inserted therein in relation to the wall surface of the associated one of the plurality of bone screw holes; and means for retaining the head portions of the at least two bone screws in associated ones of the hole inserts such that the head portions are nondisplaceable in the longitudinal direction when the head portions are in a locked condition, wherein at least one of the plurality of bone screw holes is provided with one of the hole inserts and is displaceable in the plate element.

8. A device as set forth in claim 7, wherein the displaceable bone screw hole is provided in a plate member, the plate member being displaceable relative to the plate element.

9. A device as set forth in claim 8, wherein an additional bone screw hole is provided in the plate element adjacent to the displaceable bone screw hole.

10. A device as set forth in claim 8, wherein the plate element is elongate and has two opposite ends, the plate element being provided at each end with a bone screw hole which is displaceable in a longitudinal direction of the plate element.

11. A device as set forth in claim 7, wherein an additional bone screw hole is provided in the plate element adjacent to the displaceable bone screw hole.

12. A device as set forth in claim 11, wherein the plate element is elongate and has two opposite ends, the plate element being provided at each end with a bone screw hole which is displaceable in a longitudinal direction of the plate element.

13. A device as set forth in claim 7, wherein the plate element is elongate and has two opposite ends, the plate element being provided at each end with a bone screw hole which is displaceable in a longitudinal direction of the plate element.

14. A device as set forth in claim 7, wherein the head portion of each of the at least two bone screws is cylindrical and is provided with an annular bead, and an inner surface of an associated one of the hole inserts is cylindrical and is provided with an annular recess, the annular recess matching and receiving the annular bead.

15. An implant device, comprising:

a plate element, the plate element including a plurality of bone screw holes;

annular hole inserts provided in at least two of the plurality of bone screw holes;

at least two bone screws, the at least two bone screws each having a head portion that is insertable, in a longitudinal direction of the bone screw, in an a hole insert of an associated one of the plurality of bone screw holes and lockable and unlockable relative to the hole insert;

the hole inserts each having a convex, substantially spherical, outer annular surface, the outer annular surface of each hole insert cooperating with a matching concave, substantially spherical wall surface of an associated one of the plurality of bone screw holes such that when one of the at least two bone screws is inserted in an associated one of the plurality of bone screw holes, the one of the at least two bone screws is movable to different positions relative to the plate element by rotating or tilting the hole insert and the one of the at least two bone screws inserted therein in relation to the wall surface of the associated one of the plurality of bone screw holes, wherein at least one of the plurality of bone screw holes is located at an end of the plate element and is provided with one of the hole inserts and is displaceable in the plate element.

16. A device as set forth in claim 15, wherein the head portion of each of the at least two bone screws is cylindrical and is provided with an annular bead, and an inner surface of an associated one of the hole inserts is cylindrical and is provided with an annular recess, the annular recess matching and receiving the annular bead.

17. A device as set forth in claim 15, wherein the displaceable bone screw hole is provided in a plate member, the plate member being displaceable relative to the plate element.

18. A device as set forth in claim 15, wherein the plate element is elongate and has two opposite ends, the plate element being provided at each end with a bone screw hole which is displaceable in a longitudinal direction of the plate element.

* * * * *